US00PP09402P

United States Patent [19]

Davidson

[11] Patent Number: Plant 9,402

[45] Date of Patent: Dec. 19, 1995

[54] HYBRID TEA ROSE PLANT NAMED 'HADLACE'

[76] Inventor: Harvey D. Davidson, #3 El Verano Rd., Orinda, Calif. 94563

[21] Appl. No.: 382,860

[22] Filed: Feb. 3, 1995

[51] Int. Cl.[6] ..... A01H 5/00

[52] U.S. Cl. ..... Plt./14

[58] Field of Search ..... Plt./1, 11, 14, Plt./15

*Primary Examiner*—Howard J. Locker

[57] ABSTRACT

A new rose cultivar of the Hybrid Tea class characterized by having medium sized cream, quartered, rosette shaped, flat, fragrant flowers on a bush of moderate vigor. This plant has been designated as 'Hadlace'. It will be marketed in the USA under the tradename of 'Olde Lace'.

1 Drawing Sheet

The present invention relates to a new and distinctive cultivar of rose plant of the Hybrid Tea class, which was originated by my crossing ((*Pink Favorite*×(*Polly*×*Peace*)) as the seed parent with the same pollen parent ((*Pink Favorite*×(*Polly*×*Peace*)).

Among the novel characteristics possessed by the new cultivar which distinguish it from:

(a) All other cultivars of which I am aware are:

(1) A cream flower with shadings of yellow on inner petals.

(2) Old rose form being quartered, roseette and flat.

(3) Fully petalled.

(4) Very disease resistant.

(b)

*Seed parent.*—Large, high centered, yellow flowers.

*Pollen parent.*—Same as seed parent.

Asexual reproduction of the new rose cultivar by budding, as performed at Tulare, Calif. shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers in the aformentioned color chart, e.g. "53A" is plate "53A" of The Royal Horticultural Society Colour Chart.

Parentage:

*Seed parent.*—((*Pink Favorite*×(*Polly*×*Peace*)).

*Pollen parent.*—Same as seed parent.

Class: Hybrid Tea.

The following observations are made of specimens grown outdoors in Contra Costa County, Calif., in the month of September.

FLOWER

Blooming Habit

A. Bud:

(1) *Size.*—Sepals enclosed, 22–24 mm from base of sepals to top of bud.

(2) *Form.*—Globular.

(3) *Sepals.*—22 to 27 mm in length; 5 to 6 mm extension beyond bud; no serration shown on sepal edges. Generally 3 out of 5 sepals show appendages on each side, 2 to 4 mm length. Sepals show glandular development on edges. Heavy cotton matting on inner surface, fine matting on outer surface. Outside color — 146C; inside — 195A.

(4) *Penduncle.*—Length — 6 to 7 cm. Surface — smooth, no prickles, a few glandular hairs. Strength — firm. Color — 146C.

(5) *Receptacle.*—Shape — Full, rounded: 12–14 mm diameter. Color — 146C.

(6) *Color.*—When sepals first divide, outside petals near to 158D.

B. Bloom:

(1) *Size.*—When open — 8 to 9 cm.

(2) *Borne.*—1–2 per stem.

(3) *Form.*—Globular, rounded, flat when fully open.

(4) *Petalage.*—Average — 70 to 76.

(5) *Color.*—Early open: outer petals 158D; inner petals 159B. Aging: Lightening of 158B to 158D.

C. Petals:

(1) *Texture.*—Firm.

(2) *Appearance.*—Flexed; satiny.

(3) *Form.*—Very ruffled.

(4) *Arrangement.*—Cupped rosette opening to quartered.

(5) *Petaloids in center.*—Average 50 to 60.

(6) *Persistence.*—Drop off cleanly.

(7) *Fragrance.*—Good.

(8) *Lasting quality.*—On plant 6–7 days; cut 5–6 days.

REPRODUCTIVE ORGANS

A. Stamen:

(1) *Arrangement.*—Irregular around styles.

(2) *Number.*—Average 50–55.

(3) *Length.*—Average — 4 to 10 mm.

(4) *Filaments.*—Color — Close to 18D.

(5) *Anthers.*—Color — Close to 21D.

(6) *Pollen.*—22D.

Pistil:

(1) *Styles.*—Length: 9–12 mm exposed; number: 100 to 105; color: near to 155B; sparsely coated with white hairs.

(2) *Stigma.*—Color — Close to 9D.

(3) *Overy.*—Shape — round; 10 mm center cross-section at sepal base.

C. Hips: Does not set seed.

PLANT

A. Form: Upright.

B. Growth: Moderate.

*Height.*—Average 80 cm.

C. Stem length:

*Basal break to flower bud tip.*—Average — 60 to 70 cm.

D. Foliage: Compound of 3 to 5 leaflets on bloom stem; 5 to 7 leaflets on main canes.

(1) *Mature size.*—5 leaflet — tip of leaflet to stipule base 10–12 cm.

(2) *Quantity.*—Stems well covered.

(3) *Color.*—New foliage upper side close to 139C; under side 139D. Old foliage upper side 137A, under side 137C.

(4) *Shape.*—Oval with center pointed.

(5) *Texture.*—Firm, leathery, slightly glossy.

(6) *Edge.*—Slight serration on outer edge. Average 5 points per 1 cm, with up to 1 mm peak.

(7) *Rachis.*—Glandular hair on upper side; lower side: 6 to 8 hooked prickles ½–1 mm length, spaced near to ¾ to 1 cm apart.

(8) *Stipules.*—Length 13–15 mm; auricle to 5 mm. Edge of stipule to tip of auricle with many glandular hairs.

E. Resistance to disease: Mildew, rust, blackspot: very good.

F. Wood:

*New wood.*—Color close to 137B and C. Bark — smooth.

*Old wood.*—Color close to 146A, shadings of 183B. Bark — smooth.

G. Thorns on mature wood:

*Size.*—4–8 mm.

*Number per* 10 *cm.*—Primary wood 5–6 thorns. Secondary wood 20–25.

*Shape.*—Straight, downward point.

*Color.*—Close to 183A.

H. Winter hardiness: Very good.

I claim:

1. A new and distinct rose cultivar of the Hybrid Tea class, substantially as herein shown and described.

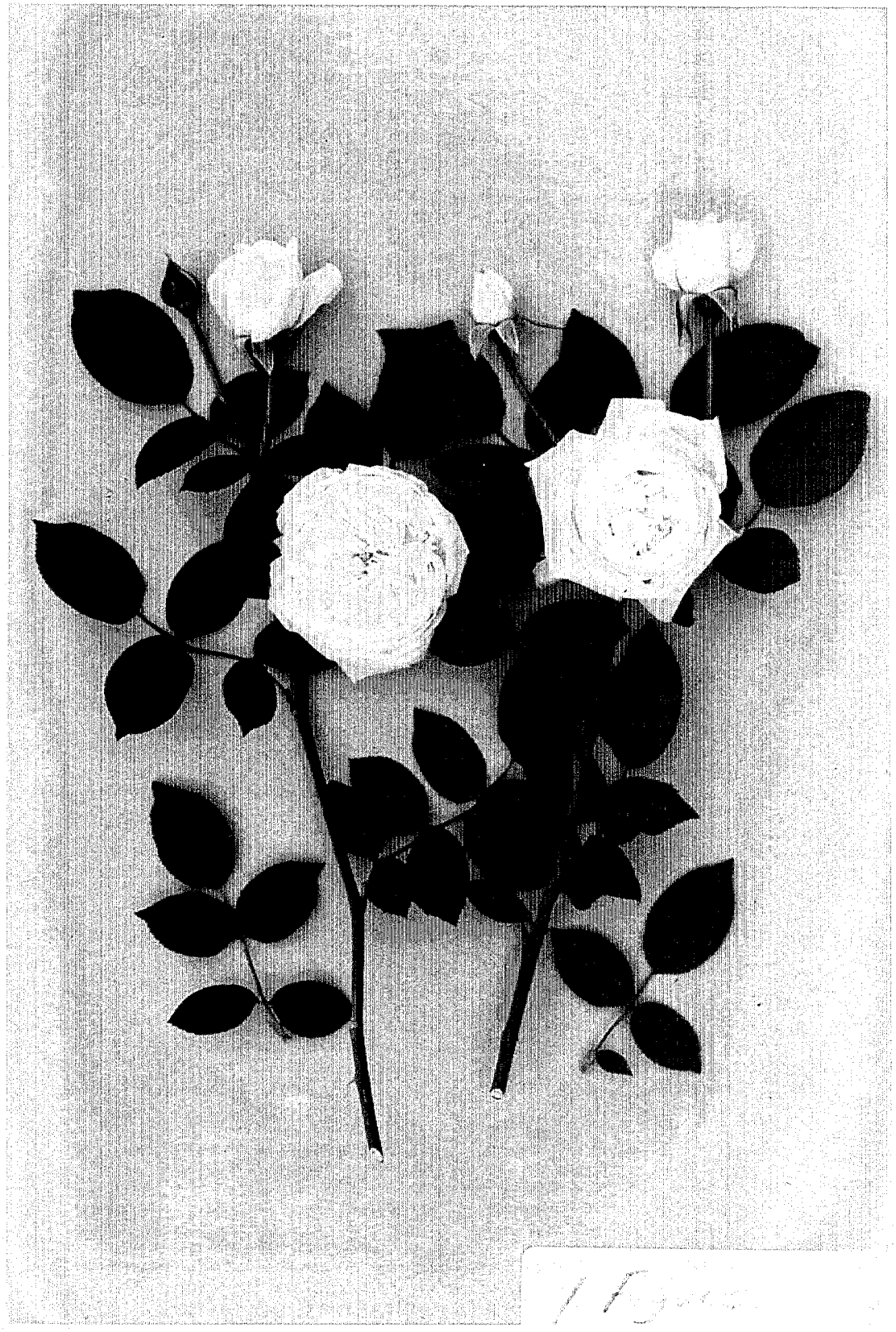

* * * * *